(12) United States Patent
Sato et al.

(10) Patent No.: US 6,582,954 B2
(45) Date of Patent: Jun. 24, 2003

(54) BIOPOLYMER DETECTOR

(75) Inventors: Keiichi Sato, Kanagawa (JP);
Mitsuhiro Tachibana, Kanagawa (JP);
Toshiki Morita, Kanagawa (JP);
Motonao Nakao, Kanagawa (JP)

(73) Assignee: Hitachi Software Engineering Co., Ltd., Kanagawa (JP)

( * ) Notice: Subject to any disclaimer, the term of this patent is extended or adjusted under 35 U.S.C. 154(b) by 0 days.

(21) Appl. No.: 10/062,132

(22) Filed: Jan. 30, 2002

(65) Prior Publication Data

US 2002/0102718 A1 Aug. 1, 2002

(30) Foreign Application Priority Data

Feb. 1, 2001 (JP) ........................................ 2001-025889

(51) Int. Cl.⁷ ................................................ C12M 1/36
(52) U.S. Cl. .............................. 435/286.2; 435/287.2; 204/403.01; 204/409
(58) Field of Search ...................... 435/285.2, 286.2, 435/287.2; 204/403.01, 409

(56) References Cited

U.S. PATENT DOCUMENTS

| | | | | |
|---|---|---|---|---|
| 4,911,794 A | * | 3/1990 | Parce et al. ................. | 205/778 |
| 5,065,106 A | | 11/1991 | Hendrick et al. ............ | 324/663 |
| 5,395,503 A | * | 3/1995 | Parce et al. ................ | 204/403.1 |
| 5,770,369 A | | 6/1998 | Meade et al. ................... | 435/6 |
| 6,428,959 B1 | * | 8/2002 | Deamer ..................... | 435/285.2 |
| 2002/0028502 A1 | * | 3/2002 | Tanaami .................... | 435/287.2 |
| 2002/0061536 A1 | * | 5/2002 | Martin et al. ................ | 435/6 |
| 2002/0064795 A1 | * | 5/2002 | Hashimoto ..................... | 435/6 |
| 2002/0086416 A1 | * | 7/2002 | Sato et al. ................. | 435/287.2 |
| 2002/0137089 A1 | * | 9/2002 | Deamer .......................... | 435/6 |

FOREIGN PATENT DOCUMENTS

| | | |
|---|---|---|
| WO | WO 98/20162 | 5/1998 |
| WO | WO 98/31839 | 7/1998 |
| WO | WO 99/67425 | 12/1999 |
| WO | WO 00/060125 | 10/2000 |
| WO | WO 01/11080 A1 | 2/2001 |
| WO | WO 01/44501 A2 | 6/2001 |

* cited by examiner

Primary Examiner—David A. Redding

(57) ABSTRACT

Disclosed is a biopolymer (DNA) detector capable of performing overall analysis including an unreacted sample without needing any complex work such as washing or the like. A DNA probe 66 is fixed to an electrode plate 22, and the electrode plate 22 is displaced by applying a DC voltage between electrode plates 22 and 23. Thus, sample DNA 63 to be detected can be separated. It becomes possible to obtain a clearer result by performing analysis based on a ratio of an entire reaction system.

7 Claims, 7 Drawing Sheets

BIOPOLYMER DETECTOR

PRIORITY INFORMATION

This application claims priority to Japanese Application Serial No. 2001-25889, filed Feb. 1, 2001.

BACKGROUND OF THE INVENTION

The present invention relates to a biopolymer detector capable of detecting presence/absence of biopolymers such as DNA, RNA, protein or the like in a sample, and measuring a present amount or a concentration thereof.

A typical method of a conventional DNA detection technology has been to modify DNA with a radioactive material, fluorescent dye or the like by using a radioactive isotope (RI), fluorescence technology or the like, excite the DNA by an external stimulus, and then observe its response based on light emission. A charge detection method has also been invented, which makes electrochemical determination by using intercalating agents specifically coupled to DNA double strands, and based on an oxidation reduction potential thereof. Moreover, as a method which needs no modification or the like, a method making use of a surface plasmon resonance phenomenon has been available. Regarding a technology for fixing DNA to an electrode, a method using a thiol-modified DNA probe or the like has been available, which utilizes an action in which a monomolecular film of a free thiol group at the tail end of the DNA forms itself on a full surface.

SUMMARY OF THE INVENTION

Among the methods made available in the conventional DNA detection technology, it was necessary to modify the DNA in case of using the RI or fluorescence technology.

The present invention provides a biopolymer (DNA) detector capable of performing direct detection by using the property of DNA without needing any modification of the DNA.

A biopolymer detector according to an aspect of the invention comprises: voltage supplying means for applying a voltage between two electrodes of a casing for housing biopolymers between the electrodes; and measuring means for measuring an electrical characteristic between the electrodes, alternatively a change in the electrical characteristic.

A biopolymer detector according to another aspect of the invention comprises: voltage supplying means for applying a voltage between two electrodes of a casing for housing biopolymers between the electrodes; electrode driving means for changing a distance between the electrodes; and measuring means for measuring an electrical characteristic between the electrodes, alternatively a change in the electrical characteristic.

The voltage supplying means can selectively supply AC or DC voltages, and can draw biopolymers to one or both of the electrodes.

The measuring means can further includes arithmetic processing means for calculating one selected from presence/absence of biopolymers between the electrodes, a present amount, a base length, a concentration, a rate of hybridization, and an amount of hybridization based on a measuring result of the electrical characteristic, alternatively a change in the electrical characteristic. Thus, various characteristic amounts of biopolymers can be measured.

Heating means can be further provided for applying heat to the electrodes to dissociate hybridized biopolymers between the electrodes into a single strand. Thus, the presence of complementary strand biopolymers and non-complementary strand biopolymers can be respectively detected.

According to the detector of the invention, it is only necessary to inject sample DNA between the opposing electrodes. According to this technology, since the amount of present DNA can be physically measured, a concentration or the like can also be measured. Moreover, in the detector, by applying the external force of an electric field to the opposing electrodes, single-strand probe DNA fixed to the electrode surface, and sample DNA that has not been hybridized are drawn to the electrode, to which the probe DNA is not fixed. Accordingly, gene detection can be carried out without needing any washing.

Furthermore, both reacted and unreacted samples are measured by employing the method of the invention. Thus, a clearer result can be obtained.

DETAILED DESCRIPTION OF THE PREFERRED EMBODIMENTS

Hereinafter, detailed description will be made for the preferred embodiment of the present invention with reference to the accompanying drawings.

Figure 1:
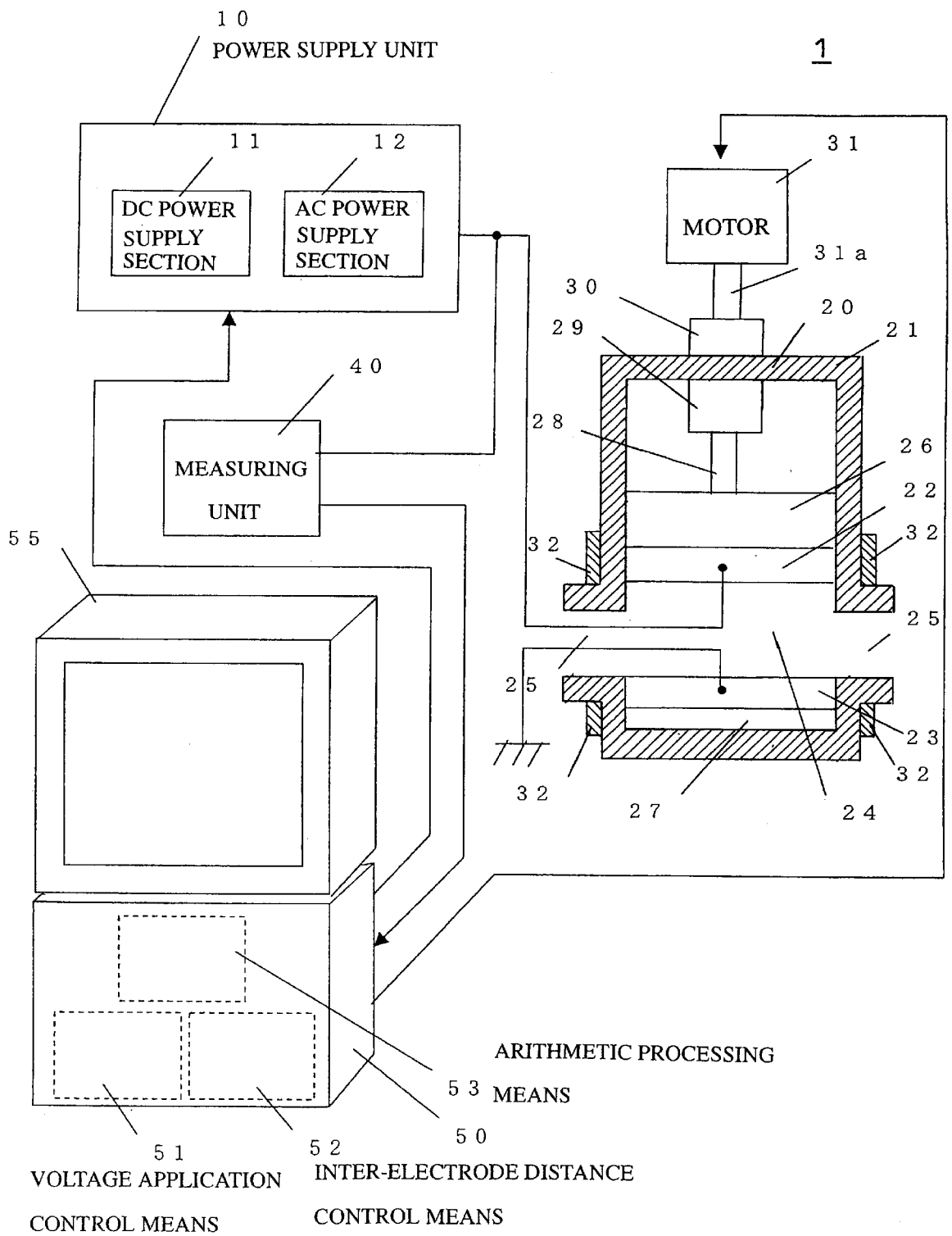
FIG. 1 is a schematic diagram showing a configuration of a biopolymer detector 1 according to an embodiment of the present invention.

FIG. 1 is a schematic diagram showing a configuration of a biopolymer detector 1 according to the embodiment of the invention.

According to the embodiment, the biopolymer detector 1 roughly comprises a power supply unit 10, an electrode plate unit 20, a measuring unit 40, and a computer 50 as control means for controlling each of these sections.

In the embodiment, the power supply unit 10 includes a DC power supply section 11 for generating a DC voltage, and an AC power supply section 12 for generating an AC voltage.

The power supply unit 10 selectively supplies/cuts off a DC voltage or an AC voltage to the electrode plate unit 20 based on a control signal from voltage application control means 51 provided in the computer 50.

The electrode plate unit 20 includes a pair of electrode plates 22 and 23 disposed opposite to each other in a cylinder-shaped casing 21. A space in the casing 21, which is defined between the electrode plates 22 and 23, forms a solution reservoir 24 for storing a solution prepared by using later-described biopolymers as solutes.

In the wall surface of the casing 21 around the solution reservoir 24, an opening 25 is formed for storing the solution in the solution reservoir 24, discharging the solution stored in the solution reservoir 24 to the outside thereof, or the like.

The electrode plate 22 of one side is connected to the output of the above-described power supply unit 10, while the electrode plate 23 of the other side is grounded in the embodiment. Thus, an electric circuitry including the electrode plate unit 20 as a circuit component is composed with respect to the power supply unit 10.

In FIG. 1, wires respectively connecting the power supply unit 10 with the electrode plate 22, and the electrode plate 23 with the ground are shown to be connected to the electrode plates 22 and 23 from the front sides (i.e., opposite sides) thereof through the opening 25 for convenience. In actual configuration, however, the wires are connected to the backsides or side faces of the electrode plates 22 and 23 not through the opening 25, but through another not-shown opening of the casing 21, and no wires are disposed in the solution reservoir 24.

In the case of the electrode plate unit 20 of the embodiment, the electrode plate 22 of one side has its backside inseparably attached to a movable plate 26, which is provided in the casing 21 so as to be axially displaced. Thus, the electrode plate 22 is displaced in the united manner with the movable plate 26. On the other hand, the electrode plate 23 of the other side is attached to the bottom of the casing 21 of the backside thereof so as to be fixed through an attaching member 27. Thus, the electrode plate 23 is prevented from being axially displaced in the casing 21.

A tip side of a rod 28 similarly provided in the casing 21 which is capable of axial displacement is connected to the backside of the movable plate 26, i.e., the surface of a side opposite the electrode plate 22. The base end side of the rod 28 is connected to the rotary shaft 31a of a motor 31 (e.g., stepping motor or the like) through a rotation/linear motion conversion mechanism 29 for converting a rotational motion into a linear motion, and a deceleration mechanism 30 for decelerating the rotational motion.

Here, for example, the deceleration mechanism 30 is composed of a gear connected to the rotary shaft 31a of the motor 31, and the rotational speed of the rotary shaft 31a of the motor 31 is reduced at a predetermined rate. A rotation/linear motion conversion mechanism 29 converts the rotational motion of the output shaft, not shown, of the deceleration mechanism 30 into a linear motion in the axial direction of the casing 21. The rotation/linear motion conversion mechanism 29 is composed of, for example, a cylindrical member rotated in a united manner with the not-shown output shaft of the deceleration mechanism 30, and having a screw part formed in its inner peripheral surface, and the base end side portion of the rod 28 having a screw provided in the base end side outer peripheral surface to be engaged with the inner peripheral surface screw part of the cylindrical member. By engaging the base end side of the rod 28 with the cylindrical member, and rotating the cylindrical member while the rotation of the rod 28 is regulated, the rod 28 is moved back and forth according to the rotational direction thereof. In this case, the rotation of the motor 31 is transmitted through the deceleration mechanism 30 to the cylindrical member. Thus, even without any control of the rotational amount of the motor 31 by a small rotational amount unit, the rod 28 can be moved back and forth linearly by a small distance unit. The motor 31 is controlled for driving or rotation based on a control signal outputted from inter-electrode distance control means 52 provided in the computer 50.

In addition, in the outer peripheral surface of the casing 21 around the solution reservoir 24, a heater 32 is provided as heating means. The heater 32 operates to heat a solution stored in the solution reservoir 24.

The measuring unit 40 is connected into the electric circuitry including the electrode plate unit 20 as the circuit component, and adapted to measure an electrical characteristic, or a change in the electrical characteristic of the electric circuitry including the electrode plate unit 20, in other words an electrical characteristic or a change in the electrical characteristic between the electrode plates 22 and 23. Here, as such an electrical characteristic, one can be selected from a voltage, impedance of resistance or the like, a frequency, and the like.

According to the embodiment, a characteristic value measured by the measuring unit 40 is supplied to arithmetic processing means 53 provided in the computer 50. The arithmetic processing means 53 analyzes the measuring result of the measuring unit 40, and the result of the analysis is displayed on a display 55.

Next, description will be made for a method for detecting biopolymers, which uses the foregoing biopolymer detector 1 of the embodiment composed as described above.

It is known that DNA as a biopolymer emits a current substantially equal to the level of an existing electroconductive polymer.

Thus, description will be made for a behavior of DNA when a solution containing DNA as a solute is stored in the solution reservoir 24 formed between the electrode plates 22 and 23 of the biopolymer detector 1, and a voltage is applied between the electrode plates 22 and 23.

Figure 2:
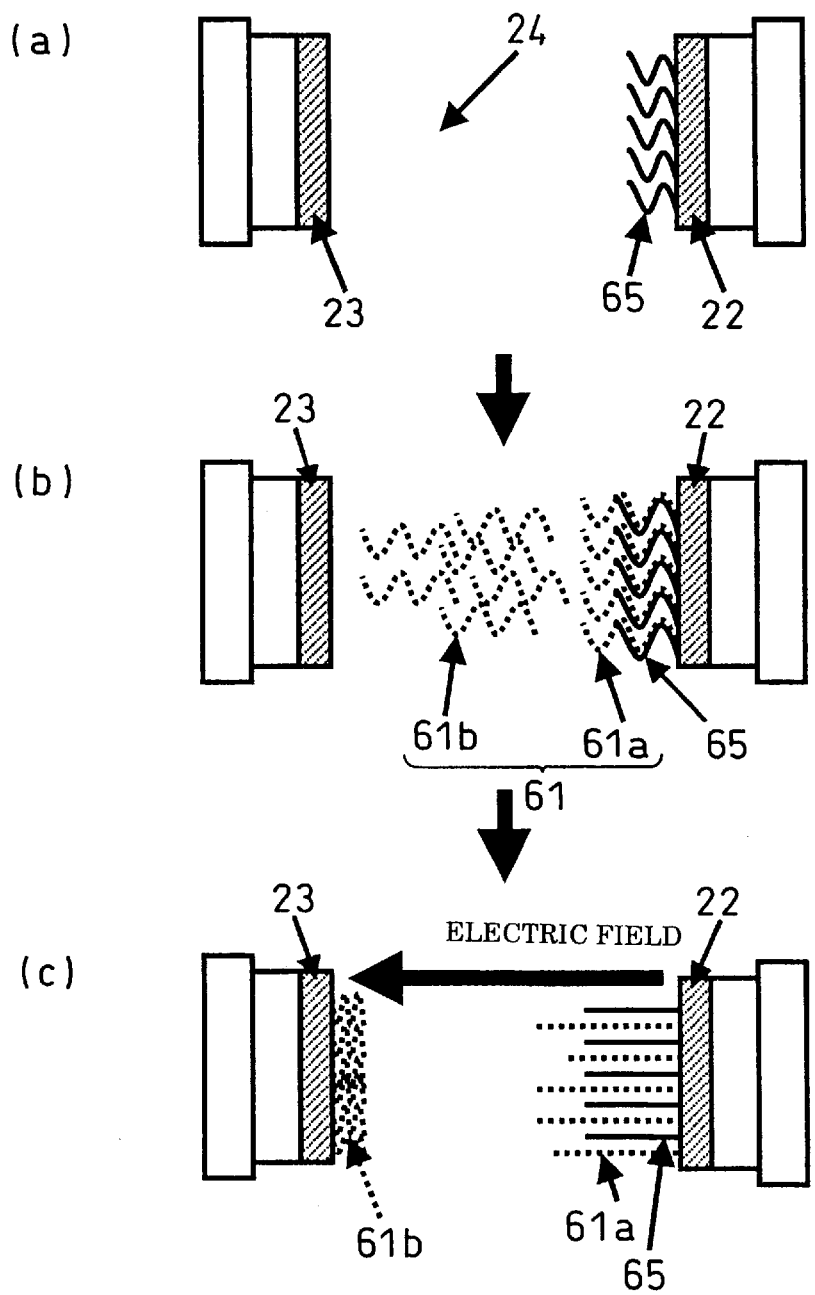
FIGS. 2(a) to 2(c) are views, each showing a behavior of DNA 61 when a DC voltage is applied between electrode plates 22 and 23.

Each of FIGS. 2(a) to 2(c) shows a behavior of DNA 61 when a DC voltage is applied between the electrode plates 22 and 23.

When a DC voltage is applied between the electrode plates 22 and 23, the DNA 61 is pulled in an electric field direction shown by an arrow in the drawing, and drawn to one electrode plate (the electrode plate 23 in this case) side.

Thus, as shown in FIG. 2(a), probe DNA 65 is fixed to the electrode plate 22, and a solution containing sample DNA 61 as a solute is stored in the solution reservoir 24 formed between the electrode plates 22 and 23. Then, as shown in FIG. 2(b), a DC voltage is applied after hybridization reaction. Subsequently, as shown in FIG. 2(c), hybridized complementary strand sample DNA 61a is extended because it is coupled to the probe DNA 65 at the electrode plate 22 side. However, non-complementary strand sample DNA 61b that has not been hybridized is drawn to the electrode plate 23 side, and contracted.

Therefore, in this state, by using the measuring unit 40 to measure an electrical characteristic such as electrical energy or the like between the electrode plates 22 and 23, it is possible to detect presence/absence of the hybridized complementary strand sample DNA 61a, and measure the present amount.

Figure 3:
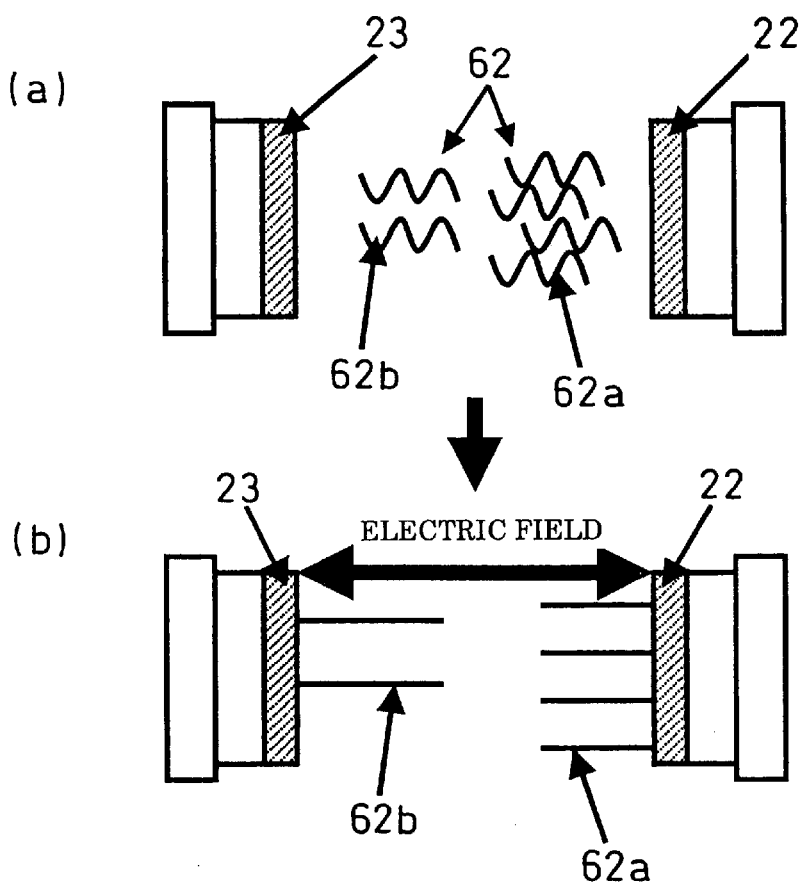
FIGS. 3(a) and 3(b) are views, each showing a behavior of DNA 62 when an AC voltage is applied between the electrode plates 22 and 23.

Each of FIGS. 3(a) and 3(b) shows the behavior of DNA 62 when an AC voltage is applied between the electrode plates 22 and 23.

As shown in FIG. 3(a), a solution containing DNA 62 as a solute is stored in the solution reservoir 24 formed between the electrode plates 22 and 23.

When an AC voltage is applied between the electrode plates 22 and 23, by a frequency and a voltage within certain ranges ($10^6$ V/m, and 1 MHz in the present device), as shown in FIG. 3(b), the DNA 62 is drawn from a position immediately before the voltage application to either side of the electrode plates 22 and 23 located nearer in its extended state. In FIGS. 3(a) and 3(b), a reference numeral 62a denotes the DNA 62 positioned not in the electrode plate 23 but in the electrode plate 22 side; 62b DNA 62 positioned in not in the electrode plate 22 but in the electrode plate 23 side.

Therefore, in the state where the solution containing the DNA 61 and 62 as solutes in the solution reservoir 24 formed in the electrode plates 22 and 23, it is possible to control the positions of the DNA 61 and 62 by properly using DC and AC voltages to be applied between the electrode plates 22 and 23.

In addition, accordingly, regarding an electrical characteristic, or a change in the electrical characteristic of the electric circuitry including the electrode plate unit 20, in other words, an electrical characteristic or a change in the electrical characteristic between the electrode plates 22 and 23, it is possible to change the electrical characteristic between the electrode plates 22 and 23, between a case containing DNA 61a and 62 in the solution stored between the electrode plates 22 and 23, and a case containing no such DNA.

Now it is assumed, for example, that the electrical characteristic between the electrode plates 22 and 23 can be measured beforehand in the case containing DNA 61a and 62 in the solution stored between the electrode plates 22 and 23, or the case containing no such DNA, and established as a condition for comparison. In this case, by relatively comparing the result of measuring the electrical characteristic in the case containing no DNA 61a or 62 (or the case of containing such DNA) with the result of measurement to satisfy the condition for comparison, it is possible to detect the case containing no DNA 61a or 62 (or the case containing such DNA).

Next, description will be made for another method for detecting DNA, which uses the biopolymer detector 1 of the embodiment, and to which the foregoing DNA position control is applied.

Each of FIGS. 4(a) to 4(f) shows a first detection example by the biopolymer detector 1 of the embodiment, to which the DNA position control is applied.

This detection example is one, where DNA 63 in the solution stored between the electrode plates 22 and 23 is extended by applying a DC voltage between the electrode plates 22 and 23, and a distance between the electrode plates 22 and 23 is controlled by driving and controlling the motor 31, thus detecting various DNA 63a, 63b and 63c having different base lengths by differentiating them from one another.

Figure 4:
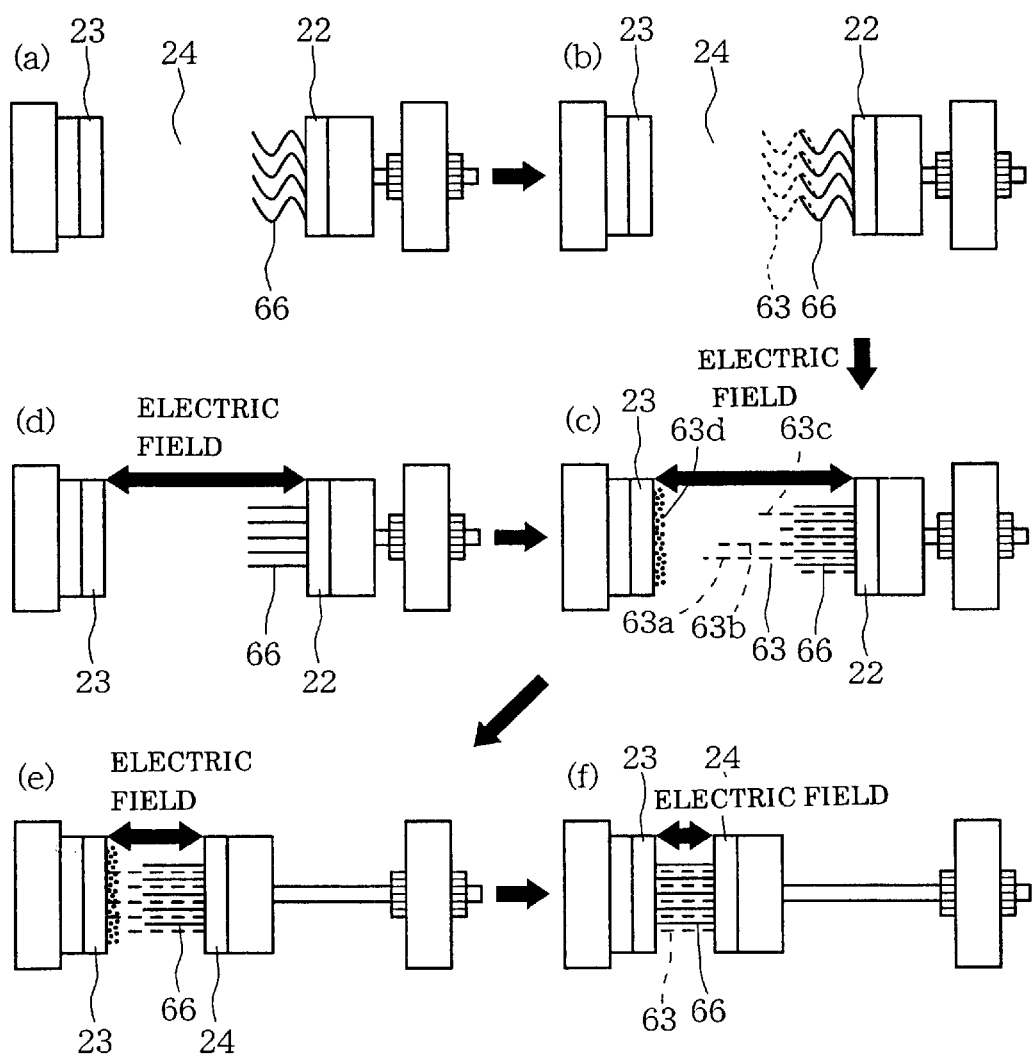
FIGS. 4(a) to 4(f) are views, each showing a first detection example by the biopolymer detector 1 of the embodiment, to which DNA position control is applied.

In the detection example, as shown in FIG. 4(a), a single-strand DNA probe 66 having a specific base sequence is fixed to one of the opposing electrode plates 22 and 23, i.e., the electrode plate 22.

On the other hand, in the solution reservoir 24 between the electrode plates 22 and 23a, a solution containing sample DNA 63 denatured into a single strand as a solute is stored. As shown in FIG. 4(b), the sample DNA 63 is hybridized with the above-described single-strand DNA probe 66.

Then, an electric field is generated between the electrode plates 22 and 23 by driving and controlling the power supply unit 10 and, as shown in FIG. 4(c), the single-strand DNA probe 66 and the sample DNA 63 denatured into a single-strand are extended.

The hybridization of the sample DNA 63 with the single-strand DNA probe 66 may be performed in the following manner. That is, as shown in FIG. 4(d), a DC voltage is applied between the electrode plates 22 and 23, and the sample DNA 63 is mixed in a solvent of the extended single-strand DNA probe 66. Then, hybridization reaction is caused between the single-strand DNA probe 66 and the sample DNA 63a, 63b and 63c in their extended states. Thus, a state like shown in FIG. 4(c) is realized.

In the above state, it is assumed that a distance d between the electrode plates 22 and 23 is maintained at an initially set distance d0 properly set beforehand, based on the base lengths of the single-strand DNA probe 66 and the sample DNA 63 denatured into a single strand.

In a state shown in FIG. 4(d), sample DNA 63d that has not been hybridized with the single-strand DNA probe 66 fixed to the electrode plate 22 is drawn to the electrode plate 23 to be deposited. Thus, this sample DNA 63d has no direct influence on detection. In other words, no washing is necessary in a detection process.

Then, in the present detection example, from the above-described state, the stepping motor 31 is driven and controlled to bring the electrode plate 22 closer to the electrode plate 23 side for small distances. Accordingly, the distance d between the electrode plates 22 and 23 is reduced for small distances to the initially set distance d0.

Then, following the reduction of the distance d between the electrode plates 22 and 23 like shown in FIG. 4(e) or 4(f), electrical characteristics such as a voltage, impedance of resistance or the like, a frequency, and the like for each distance are sequentially measured by the measuring unit 40. By comparison of time-wise changes in the measured values of such electrical characteristics, or momentary measured values, genes, i.e., biopolymers, are detected.

Figure 5:
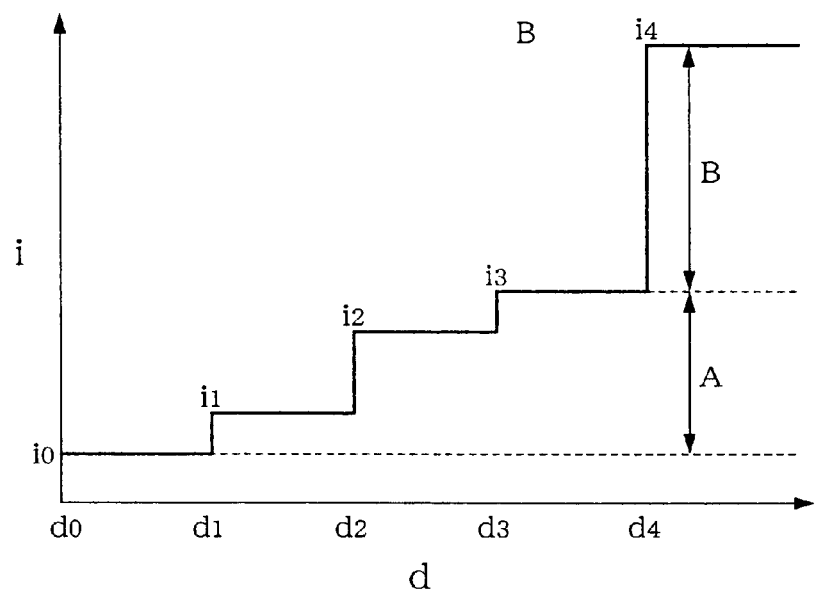
FIG. 5 is a view showing an example of a detection result obtained from an electrical characteristic between the electrode plates 22 and 23, for example a result of measuring a current i flowing between the electrode plates 22 and 23, in the first detection example.

FIG. 5 shows an example of a detection result obtained from an electrical characteristic between the electrode plates 22 and 23, for example the result of measuring the current i flowing between the electrode plates 22 and 23.

This example of the detection result is a simple representation of a relationship between the distance d between the electrode plates 22 and 23 and the current i flowing between the electrode plates 22 and 23 measured by the measuring unit 40, the distance d being taken as the abscissa, and the current i as the ordinate.

In FIG. 5, when the distance d between the electrode plates 22 and 23 is d0, neither of the tips of the sample DNA 63 denatured into a single strand and the single-strand DNA probe 66 drawn to the electrode plate 22 and set in the extended states as shown in FIG. 4(c) are not in contact with the electrode plate 23.

Accordingly, the current i hardly flows through the electrode plate unit 20, and the size of the current i measured by the measuring unit 40 is i0 (nearly 0).

Then, the distance d between the electrode plates 22 and 23 becomes d1 (d1<d0), and only the tip of the sample DNA 63a having the longest base length among the sample DNA 63 shown in FIG. 4(c) is brought into contact with the electrode plate 23. Different from the sample DNA 63a, when the sample DNA 63b and the sample DNA 63c having shorter base lengths are not in contact with the electrode plate 23, the current i flows through the sample DNA 63a between the electrode plates 22 and 23, and the size of a current measured by the measuring unit 40 is increased from i0 to i1.

Then, when the distance d between the electrode plates 22 and 23 becomes d2 (d2<d1), and the tip of the sample DNA 63b is brought into contact with the electrode plate 23 in addition to the sample DNA 63a as shown in FIG. 4(e), the current i also flows through the sample DNA 63b between the electrode plates 22 and 23, in addition to the sample DNA 63a. Accordingly, the size of a current measured by the measuring unit 40 is increased from i1 to i2.

Then, when the distance d between the electrode plates 22 and 23 becomes d3 (d3<d2), and the tip of the sample DNA 63c having a shorter base length is brought into contact with the electrode plate 23 in addition to the sample DNA 63a and the sample DNA 63b, the current i also flows through the sample DNA 63c between the electrode plates 22 and 23, in addition to the sample DNA 63a and 63b. Accordingly, the size of a current measured by the measuring unit 40 is increased from i2 to i3.

Then, when the distance d between the electrode plates 22 and 23 becomes d4 (d4<d3), and the tip of the DNA probe 66 having a further shorter base length is brought into contact with the electrode plate 23 in addition to the sample DNA 63a, 63b and 63c as shown in FIG. 4(f), the current i also flows through the DNA probe 66 between the electrode plates 22 and 23, in addition to the sample DNA 63a, 63b and 63c. Accordingly, the size of a current measured by the measuring unit 40 is further increased from i3 to i4.

In FIG. 5, the size portion of the current i indicated by A represents a signal portion by the sample DNA 63a, 63b and 63c. The size portion of the current i indicated by B represents a signal portion by the DNA probe 66.

As a result, for example, depending on the size of the current i through the electrode plate unit 20 and the time-wise change, presence/absence or the amount of the sample DNA 63a, 63b and 63c having different base lengths or the like can be calculated. Also, depending on the distance d between the electrode plates 22 and 23 when a conspicuous change occurs in the size of the current i, the base length or the like of each sample DNA 63a, 63b and 63c can be calculated by the arithmetic processing means 53 provided in the computer 50.

Each of FIGS. 6(a) to 6(d) shows a second detection example by the biopolymer detector 1 of the embodiment, to which the foregoing DNA position control is applied.

Figure 6:
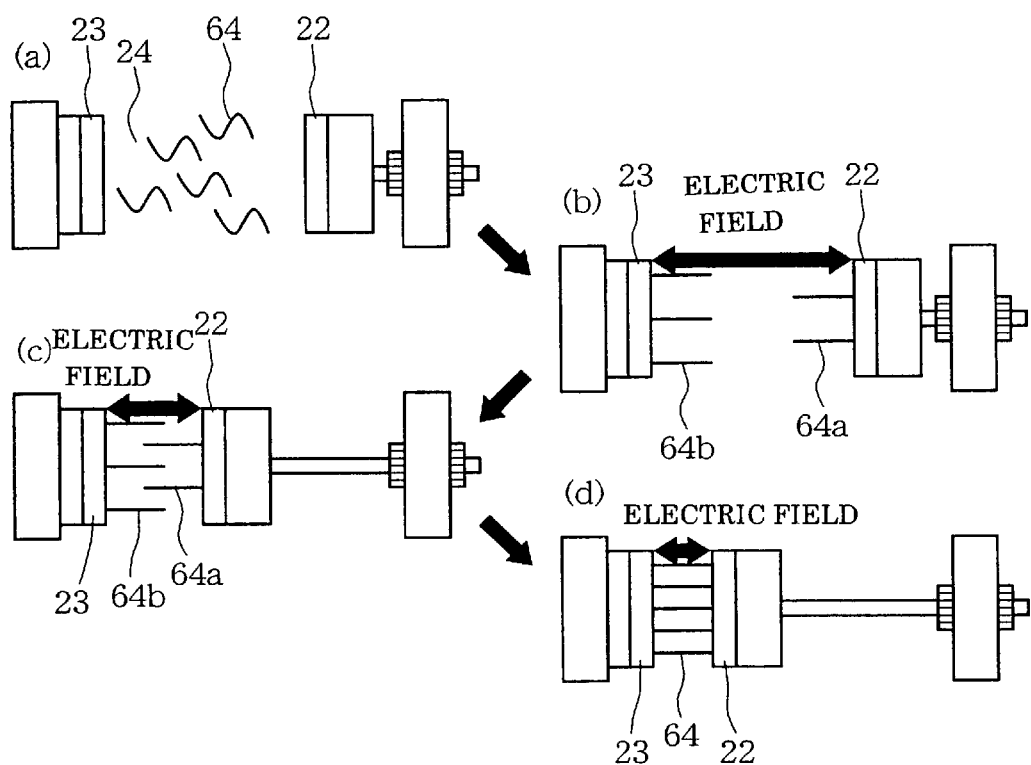
FIGS. 6(a) to 6(d) are views, each showing a second detection example by the biopolymer detector 1 of the embodiment, to which the DNA position control is applied.

In this detection example, as shown in FIG. 6(a), sample DNA 64 propagated by the polymerase chain reaction (PCR) is injected and stored in the solution reservoir 24 formed between the electrode plates 22 and 23, and a high frequency voltage (AC voltage) of, e.g., $10^6$ V/m and 1 MHz is applied by driving and controlling the power supply unit 10.

Accordingly, as shown in FIG. 6(b), the sample DNA 64 is drawn from a position immediately before the voltage application to either side of the electrode plates 22 and 23 located nearer in an extended state.

In the detection example, from this state, the stepping motor 31 is driven and controlled to bring the electrode plate 22 closer to the electrode plate 23 side for small distances, and the distance d between the electrode plates 22 and 23 is reduced to the initially set distance d0 for small distances.

Then, following the reduction of the distance d between the electrode plates 22 and 23 as shown in FIG. 6(c) or 6(d), electrical characteristics such as a voltage, impedance of resistance or the like, a frequency, and the like for each distance are sequentially measured by the measuring unit 40. By comparing time-wise changes in the measured values of such electrical characteristics, or momentary measured values, genes, i.e., biopolymers, are to be detected.

Figure 7:
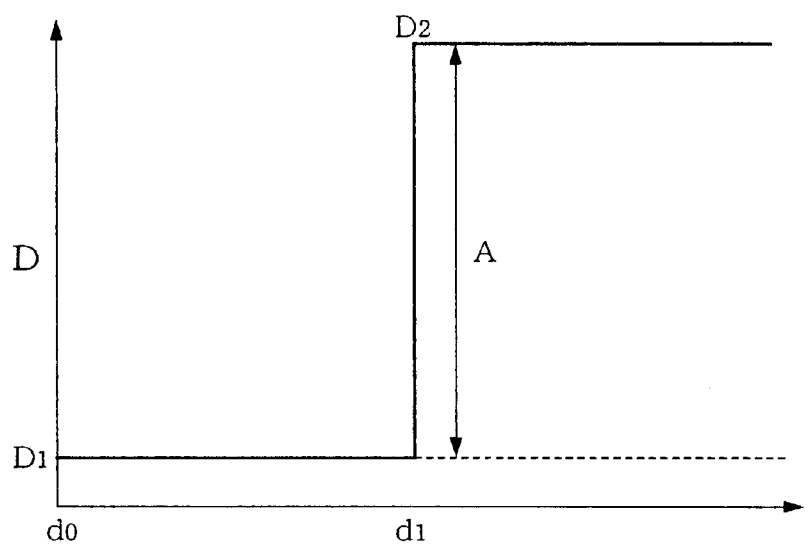
FIG. 7 is a view showing an example of a detection result obtained from a result of measuring an electrical characteristic signal between the electrode plates 22 and 23 in the second detection example.

FIG. 7 shows an example of a detection result obtained from the result of measuring an electrical characteristic signal between the electrode plates 22 and 23.

Also in this case, if only sample DNA 64a having a constant base length is present as sample DNA 64, a conspicuous increase occurs in a measured value D by changing the distance d between the electrode plates 22 and 23. Specifically, a conspicuous increase A appears in the measured value D of an electrical characteristic signal between the measured value D1 of the electrical characteristic signal when the sample DNA 64a provides no bridge between the electrode plates 22 and 23 as shown in FIG. 6(b) and 6(c), and the size D2 of the electrical characteristic signal when the sample DNA 64a provides a bridge between the electrode plates 22 and 23 as shown in FIG. 6(d).

For example, when there are one or two places of such conspicuous increase A portions, it indicates that only the DNA 64 having a constant base length is present, making it possible to confirm the success of PCR.

When there are no such conspicuous increase A portions, it indicates that no DNA are present between the electrode plates 22 and 23. In addition, when there are three or more such conspicuous increase A portions, it indicates that DNA 64a, 64b, □having different base lengths present in a number equal to the number of such conspicuous increase A portions.

Further, in the biopolymer detector 1 of the embodiment, by varying temperatures at the heater 32, the amount of DNA hybridized/non-hybridized at each temperature is measured for also making it possible to measure a single-strand dissociation temperature of DNA.

In the measurement and detection by the biopolymer detector 1 of the embodiment, the sample DNA 61 to 64 can be measured and detected in their unmodified states. To increase sensitivity, however, the sample DNA 61 to 64 may be modified by an organic or inorganic material such as fluorescent dye or the like, by applying an external stimulus or the like.

The biopolymer detector 1 of the embodiment is composed in the foregoing manner. However, the structure of the power supply unit 10 as voltage supplying means, the structure as electrode driving means including the rotation/linear motion conversion mechanism 29, the deceleration mechanism 30, the motor 31, and the like, and the detection structure of the measuring unit 40 as measuring means, are not limited to the foregoing structures. Various modifications can be employed, for example by using a linking mechanism as electrode driving means, or by using an electromagnet in place of the motor, and others.

According to the biopolymer detector of the invention, presence/absence of biopolymers such as DNA, RNA, protein or the like, a present amount, or a concentration in a sample can be easily measured without modifying the biopolymers.

What is claimed is:
1. A biopolymer detector comprising:
   voltage supplying means for applying a voltage between two electrodes of a casing for housing biopolymers between the electrodes;
   electrode driving means for changing a distance between the electrodes; and measuring means for measuring an electrical characteristic between the electrodes or a change in the electrical characteristic while the distance between the electrodes is changing time-wise in a predetermined pattern.

2. The biopolymer detector according to claim 1, wherein the voltage supplying means selectively supplies AC or DC voltages.

3. The biopolymer detector according to claim 1, wherein the measuring means further includes arithmetic processing means for determining presence/absence of biopolymers between the electrodes so as to then calculate at least one of a present amount, a base length, a concentration, a rate of hybridization, and an amount of hybridization based on a measuring result of the electrical characteristic or the change in the electrical characteristic of the biopolymers.

4. The biopolymer detector according to claim 1, further comprising: heating means for applying heat to the electrodes to disassociate hybridized biopolymers between the electrodes into a single strand.

5. The biopolymer detector according to claim 1, wherein the biopolymers have different base lengths.

6. The biopolymer detector according to claim 1, wherein the distance between the electrodes is narrowed at a constant rate.

7. The biopolymer detector according to claim 6, wherein the electrical characteristic or the change in the electrical characteristic is measured momentarily.

* * * * *